United States Patent [19]

Vichnevetskaia et al.

[11] Patent Number: 5,589,437
[45] Date of Patent: Dec. 31, 1996

[54] METHOD OF USING 5-HYDROXYBENZIMIDAZOLE COMPOUNDS FOR REDUCING TRANSPIRATION IN PLANTS

[76] Inventors: Klara D. Vichnevetskaia, Faculty of Forestry, University of Toronto, 33 Wilcoks St.; Terence J. Blake, Faculty of Forestry, University of Toronto, both of Toronto, Ontario, Canada, M5S 3B3; Eddie Bevilacqua, 3 Rutherford Avenue, Toronto, County of York, Province of Ontario, Canada, M6M 2C5; Timothy J. B. Boyle, City of Bogor, Province of West Java, Indonesia

[21] Appl. No.: 258,806

[22] Filed: Jun. 13, 1994

[51] Int. Cl.⁶ .......................... A01N 43/40; A01N 43/52; A01N 43/84; A01N 43/90
[52] U.S. Cl. .................... 504/225; 504/248; 504/253; 504/276
[58] Field of Search .................... 504/276, 225, 504/248, 253

[56] References Cited

U.S. PATENT DOCUMENTS

| | | | |
|---|---|---|---|
| 3,791,839 | 2/1974 | Cushman et al. | 106/268 |
| 3,826,671 | 7/1974 | Petrucco et al. | 117/3 |
| 3,847,641 | 11/1974 | Cushman et al. | 117/3 |
| 4,645,682 | 2/1987 | Elmore | 427/4 |
| 4,671,816 | 6/1987 | Bliesener et al. | 71/122 |
| 4,943,315 | 7/1990 | Schulz et al. | 71/120 |

FOREIGN PATENT DOCUMENTS

| | | |
|---|---|---|
| 1098934 | 6/1984 | U.S.S.R. . |
| 1282492 | 3/1985 | U.S.S.R. . |
| 1253559A1 | 8/1986 | U.S.S.R. . |
| 1470235A1 | 4/1989 | U.S.S.R. . |

OTHER PUBLICATIONS

Pp. 63–68 and 155–157 from a text entitled Tree Growth and Environmental Stresses (University of Washington Press, Seattle and London, published 1979).

McCutcheon's vol. 1: Emulsifiers & Detergents (North American Edition), pp. 275–297, published 1993 by McCutcheon Division, MC Publishing Company, 175 Rock Road, Glen Rock, NJ 07452, U.S.A.

McCutcheon's vol. 1: Emulsifiers & Detergents (International Edition), pp. 247–268 & 271, published 1993 by McCutcheon Division, MC Publishing Company, 175 Rock Road, Glen Rock, NJ 07452, U.S.A.

CA 118: 187,907, Vishnevetskaia et al, Abstract of "Genectic Polymorphism of Proteins and Regulation of Pine Growth" *Izv. Ross. Akad. Nauk* 5:807–10. 1992.

*Primary Examiner*—S. Mark Clardy

[57] ABSTRACT

It has been discovered that certain hydroxybenzimidazole compounds provide beneficial characteristics to certain agricultural species. Treatment of certain plants with an effective amount of the hydroxybenzimidazole compounds of the present invention has been observed to cause an increase in water use efficiency of plants thus treated, which reduces plant transpiration.

Hydroxybenzimidazole compounds of the present invention are thus beneficial and useful for improving plant resistance to drought.

8 Claims, No Drawings

METHOD OF USING 5-HYDROXYBENZIMIDAZOLE COMPOUNDS FOR REDUCING TRANSPIRATION IN PLANTS

TECHNICAL FIELD OF THE INVENTION

Our invention, in general, is directed to a method for improving plant drought tolerance by reducing the transpiration rate of plants.

Our novel method, more particularly, contemplates applying an effective amount of an anti-transpirant compound to certain plants.

The practice of our novel method has been observed to result in an increase in the ability of certain plant seedlings to survive drought, and to increased plant yields of treated agricultural species.

BACKGROUND OF THE INVENTION

It is axiomatic that efficient utilization of water—for agricultural as well as for virtually all other purposes—is desired by most of the world's population. For example, not only is efficient utilization of water essential to obtain optimal crop yields, the efficient utilization of agricultural water is known to impact upon navigable water systems, potable water sources and supplies, water for industrial uses, and water for recreational uses.

It is well known that virtually all plants require a certain quantity of water for proper growth and development.

Drought limits the productivity of virtually all plants.

Moreover, the ability of various plant seedlings to survive drought is currently thought to be influenced by chemical as well as environmental pre-treatments.

In any event, it is also well known—with respect to many plant species—that a significant quantity of water absorbed from soil returns to the atmosphere via plant transpiration. In particular, the loss of water through transpiration may be so undesirable as to limit key metabolic processes associated with plant growth and development.

Optimizing water utilization of plants is thus desirable, particularly if the plant is known to possess a commercial agricultural value.

While placing a physical barrier over plant stomata is known to reduce water lost via transpiration, the procedure is not always desirable.

For example, physical barriers over plant stomata may inhibit certain gas-exchange processes of the plant. It would be much more desirable to enable the plant to use more efficiently the water it receives.

In U.S. Pat. No. 4,645,682 to Elmore there is disclosed a method and composition, said to be able to protect a plant from weather-induced damage. Disclosed is a composition said to comprise an aqueous solution containing a dark-hued vegetable dye, an anti-transpiration agent, an agricultural streptomycin, and complexed mineral micronutrients.

The dye is said to be effective for shading the leaves of a plant from the effects of sunlight. The streptomycin is said to be effective for suppressing growth of certain fungus. The micronutrients are said to be effective for promoting plant growth and function.

The anti-transpiration agent is said to be effective for limiting transpiration of water from the plant. In the sole example of the Elmore patent, aqueous paste wax is disclosed as the anti-transpiration agent; while certain other anti-transpiration agents—i.e. those disclosed in each of the U.S. Pat. Nos. 3,791,839; 3,826,671; and 3,847,641—are incorporated by reference into the Elmore patent.

U.S. Pat. Nos. 3,791,839 and 3,847,641, both to Cushman et al., each disclose wax emulsions which are said to be useful for controlling transpiration in plants.

U.S. Pat. No. 3,826,671 to Petrucco et al. discloses a composition said to be effective for controlling transpiration in plants, the composition comprising a polymer, an emulsifier, and water.

In U.S. Pat. No. 4,671,816 to Bliesener et al. there is disclosed an acetylene compound, said to possess utility for regulating plant growth.

Russian patent document SU 1 282 492 to Kuznetsov et al. discloses 2-methyl-4,6-bis(dimethylaminomethyl)-5-hydroxybenzimidazole hydrochloride, which is said to possess plant growth regulator activity.

In Russian patent document SU 1 098 934 to Smirnov et al. there are disclosed 4-aminomethyl derivatives of 2-methyl-5-hydroxybenzimidazole, which are said to possess plant growth regulator activity.

Russian patent document SU 1 253 559 A1 to Kuznetsov et al. discloses 2-methyl-4-dimethylaminomethyl-5-hydroxybenzimidazole hydrobromide, which is said to possess growth-stimulating activity for coniferous tree species.

In Russian patent document SU 1 470 235 A1 to Vishnevetskaia et al. a method is disclosed for determining the sensitivity of certain genetic families of coniferous tree species to the action of a growth-stimulating preparation. In particular, results obtained for the effect of 2-methyl-4-dimethylaminomethyl-5-hydroxybenzimidazole dihydrochloride on the morphological parameters of pine seedlings are shown.

In a document entitled "Ambiol," Stoljarova et al. disclose a plant growth regulator, said to be an anti-stress anti-oxidant of complex effect, possessing anti-mutagenical and radio-protective properties.

In U.S. Pat. No. 4,943,315 to Schulz et al. there are disclosed formulations which are said to possess utility as agents for reducing transpiration in plants and/or for avoiding impairment to plants caused by heat and dry conditions. Such formulations are said to comprise an acetylene as well as a phenylbenzylurea, each of specified structure.

Through the years, those skilled in the art have shown an interest in maintaining a favorable water balance by applying "anti-transpirant" agents (also called "anti-desiccants") to leaves. Such anti-transpirants typically fall into two recognized categories: the "film-type" and the "metabolic" anti-transpirants. Film-type anti-transpirants form a film on leaves, thereby either blocking stomatal pores, or coating leaf epidermal cells with a water-proof film. Typical film-type anti-transpirants include waxes, wax-oil emulsions, higher alcohols, silicones, plastics, latexes and resins. Metabolic anti-transpirants chemically close stomatal pores. Typical metabolic anti-transpirants include succinic acids, phenylmercuric acetate, hydroxysulfonates, the herbicide atrazine, sodium azide, and phenylhydrazones, as well as carbon cyanide.

Anti-transpirants of these sorts have either exhibited phytotoxic effects or inhibited plant growth, as is discussed and shown by T. T. Kozlowski at pages 155–157 in the text entitled *Tree Growth and Environmental Stresses* (Univ. of Washington Press, Seattle and London, published 1979).

Unlike known prior-art procedures, the anti-transpiration methods of our invention do not involve application to leaves (otherwise referred to as "foliar treatment"). On the contrary, and as will be shown in examples presented below, improved water-use efficiency and increased biomass of plant species treated with the formulations of this invention have resulted either from treatment of seeds or from application to plant root systems.

It would be beneficial to limit transpiration rates, thereby to foster an increase in carbon gain rates per unit of water transpired, the term also being referred to as water-use efficiency ("WUE").

An increase in water-use efficiency would tend to stimulate plant growth under mild drought conditions.

It is thought that trees with higher "WUE" values would dry out soils more slowly and use less water, and that lower plant transpiration rates would cause an increase in plant growth rates by reducing stress levels in plant leaves.

SUMMARY OF THE INVENTION

It has been discovered that certain derivatives of hydroxybenzimidazole provide beneficial characteristics to various agricultural species.

More particularly, it has been discovered that such derivatives of hydroxybenzimidazole are clearly beneficial and useful, in that such derivatives of hydroxybenzimidazole improve resistance to drought.

Still more particularly, it has been observed that treatment of a particular plant seed or root system with an effective amount of the hydroxybenzimidizole derivatives which are the subject of the present invention causes an increase in water use efficiency of the plant, thereby causing a reduction in plant transpiration.

The hydroxybenzimidazole derivatives that are the subject of our present invention are of the structure

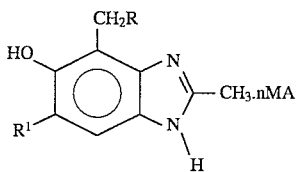

wherein nMA connotes that the hydroxybenzimidazole derivative structurally presented above is a mineral acid salt; wherein n is an integer 1 through 6, more preferably 1 or 2, most preferably 2; wherein MA is a mineral acid selected from the group consisting of $HNO_3$, $H_2SeO_4$, $HClO_4$, $HBrO_4$, $HMnO_4$, $HSO_3F$, $H_2SO_4$, $H_2S_2O_7$, $H_3PO_4$, $H_3BO_3$, HF, HCl, HBr, HI, and mixtures thereof; wherein MA is a mineral acid preferably selected from the group consisting of HCl and HBr; wherein MA is most preferably the mineral acid HCl; wherein R is selected from either hydrogen, dimethylamino, piperidinyl or morpholino; and $R^1$ is selected from hydrogen or dimethylaminomethyl.

A preferred hydroxybenzimidazole for use in the practice of our present invention is the compound wherein R is dimethylamino and $R^1$ is hydrogen. Such a hydroxybenzimidazole derivative, also known by the name "Ambiol," mentioned above, is more particularly characterized as 2-methyl-4-(dimethylaminomethyl)-5-hydroxybenzimidazole dihydrochloride.

Further aspects of our present invention are directed to the use of 2-methyl-4-(dimethylaminomethyl)-5-hydroxybenzimidazole dihydrochloride as an effective anti-transpirant in various woody species, such as trees.

In addition, data appearing below will show the anti-transpirant benefits of our present invention to be effective in connection with agriculturally-significant products, such as grains and legumes.

In connection with still another aspect of our present invention, a process for increasing the water utilization of various plant species is set forth. In such a process, there is minimal physical blockage of plant stomata (which would tend to decrease transpiration), but instead there is a metabolic effect upon the plant, which tends to increase water utilization by the plant, thereby affording the plant its usual and normal gas-exchange or carbon-fixation processes through the leaf epidermis.

Yet another aspect of our present invention is directed to the biomass increase of the species treated. Such biomass increase is a benefit which is achieved as a result of improved water efficiency by the plant. Such an increase in biomass is of economic importance, in general, and is of agricultural interest to commercial farmers, in particular.

Other aspects, features and advantages of our present invention are discussed in greater detail below.

INDUSTRIAL APPLICABILITY

The principal utility of our present invention is in the field of agriculture. Specific examples are set forth below.

DETAILED DESCRIPTION OF THE INVENTION

Our method for reducing transpiration in plants utilizes an effective amount of a hydroxybenzimidazole derivative of the following structure:

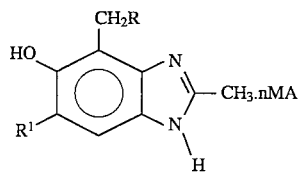

wherein nMA connotes that the hydroxybenzimidazole derivative structurally presented above is a mineral acid salt; wherein n is an integer 1 through 6, more preferably 1 or 2, most preferably 2; wherein MA is a mineral acid selected from the group consisting of $HNO_3$, $H_2SeO_4$, $HClO_4$, $HBrO_4$, $HMnO_4$, $HSO_3F$, $H_2SO_4$, $H_2S_2O_7$, $H_3PO_4$, $H_3BO_3$, HF, HCl, HBr, HI, and mixtures thereof; wherein MA is a mineral acid preferably selected from the group consisting of HCl and HBr; wherein MA is most preferably the mineral acid HCl; wherein R is selected from either hydrogen, dimethylamino, piperidinyl or morpholino; and $R^1$ is selected from hydrogen or dimethylaminomethyl.

A preferred hydroxybenzimidazole for use in the practice of our present invention is the compound wherein R is dimethylamino and $R^1$ is hydrogen. Such a hydroxybenzimidazole derivative, also known by the name "Ambiol," mentioned above, is more particularly characterized as 2-methyl-4-(dimethylaminomethyl)-5-hydroxybenzimidazole dihydrochloride.

Methods for synthesizing 2-methyl-4-(dimethylaminomethyl)-5-hydroxybenzimidazole dihydrochloride ("Ambiol") are known in the art, and our present invention is especially concerned with the heretofore undisclosed and unknown use of this preferred hydroxybenzimidazole derivative as an anti-transpirant.

In a preferred embodiment of our present invention, an effective amount of 2-methyl-4-(dimethylaminomethyl)-5-hydroxybenzimidazole dihydrochloride was applied as a treatment to seeds.

An effective amount of 2-methyl-4-(dimethylaminomethyl)-5-hydroxybenzimidazole dihydrochloride was also applied to black spruce and jack pine seedlings. Following two months of treatment, seedlings were subjected to drought. Physiological variables—including net photosynthesis rate, transpiration rate, stomatal conductance, needle water potential ("$\Psi_{NEEDLE}$") and water-use efficiency ("WUE")—were monitored before, during, and after drought. The increase in water-use efficiency ("WUE") is demonstrated in certain examples set forth below. Promotion of seedling growth is also incidentally shown.

In another preferred embodiment, the effect of utilizing 2-methyl-4-(dimethylaminomethyl)-5-hydroxybenzimidazole dihydrochloride, with respect to growth during drought, of a number of agricultural species is demonstrated. In particular, the effects of utilizing various concentrations of 2-methyl-4-(dimethylaminomethyl)-5-hydroxybenzimidazole dihydrochloride, in connection with species subjected to drought, are presented with respect to the emergence and germination of certain agricultural and forestry species.

The traditional method of applying drought stress to plants (i.e."droughting") in soil culture is by withholding irrigation. This method tends to increase plant stress in an uncontrolled manner, resulting in a lag time between the cessation of irrigation and the development of drought conditions.

Another use for drought stress is with respect to pre-conditioning of conifer seedlings, typically done in the greenhouse.

Such pre-conditioning of conifer seedlings may enhance their survival when transplanted into the field. Pre-conditioning has typically involved the limitation of available water through the deprivation of irrigation or by subjecting the conifer roots to osmotic stress.

These techniques are difficult to regulate, are costly, and can lead to unacceptably high levels of seedling mortality.

For these reasons, it is desirable that a more advanced technique of drought imposition be employed.

One such technique is based upon "aeroponics," i.e. roots and root systems grown in nutrient mist. An "aeroponics" procedure thus allows for the routine application of a controlled degree of plant water stress.

Another method of drought-stressing a plant is brought about not by limiting plant water but by altering environmental demand for water by controlling atmospheric absolute humidity or percent relative humidity.

The 2-methyl-4-(dimethylaminomethyl)-5-hydroxybenzimidazole dihydrochloride compounds, in accordance with principles of our present invention, may advantageously be applied in effective amounts to crops either by treating seeds, or by treating roots, or by spraying leaves.

The 2-methyl-4-(dimethylaminomethyl)-5-hydroxybenzimidazole dihydrochloride compounds, in accordance with principles of our present invention, are tolerated by many commercial crop plants, and application rates thus may vary. When the active ingredient is used as a "bath" or soak to treat seeds, for example, the amount of active ingredient may vary from 0.01 milligrams per liter of water to 100 milligrams per liter of water.

The 2-methyl-4-(dimethylaminomethyl)-5-hydroxybenzimidazole dihydrochloride compounds, in accordance with principles of our present invention, can be applied in conventional formulations, such as solutions, emulsions, suspensions, dusts, powders, pastes and granules.

The formulation chosen depends entirely on the purpose for which the active ingredients are used. Any particular formulation thus chosen should ensure a fine and uniform distribution of the active ingredient.

Suitable carriers employed in connection with the anti-transpirant compositions of our present invention may be a finely-divided or granular organic or inorganic inert material.

Suitable inert carriers within the contemplation of our present invention are attapulgite, sand, vermiculite, corncobs, activated carbon and mineral silicates such as mica, talc, pyrophyllite and clay.

Yet, in still other embodiments of our present invention, the carrier that is utilized comprises a solution. In particular, when the carrier is a liquid solvent, a preselected 2-methyl-4-(dimethylaminomethyl)-5-hydroxy benzimidazole dihydrochloride compound is dissolved in a suitable solvent which acts as the carrier.

Suitable solvents in accordance with principles of our present invention include but are not limited to: acetone, methanol, isopropanol, n-butyl alcohol, tert-butyl alcohol, cyclohexanol, cyclohexanone, dioxane, dimethyl formamide ("DMF"), dimethylsulfoxide ("DMSO"), toluene, xylene, ethylene dichloride, diacetone alcohol, and N-methylpyrrolidone.

In additional embodiments of our present invention, the carrier used comprises an emulsion. Suitable emulsions include but are not limited to oil-in-water emulsions, water-in-oil emulsions, microemulsions, and dual emulsions.

To produce a water-based biologically-active formulation (which includes the active ingredient of our present invention) a suitable form of the active ingredient of our present invention may advantageously be dissolved in a suitable organic solvent into which a suitable surface-active dispersing agent has been added. Water is thereafter typically added to (or otherwise combined with) the resulting mixture, to form an aqueous emulsion. The resulting aqueous emulsion may thereafter advantageously be applied to a particular location (i.e. "locus") to be treated, one such particularly preferred method of application being spraying.

Alternatively, the emulsion may utilize an organic liquid, such as oil, as the dispersant.

The surface-active dispersing agent may be any of those known to those skilled in the art.

For purposes of our present invention, examples of suitable surface-active agents are listed on pages 275–297 of *McCutcheon's* 1993 *Emulsifiers & Detergents* (Volume 1) North American Edition and on pages 247–268 and 271 of *McCutcheon's* 1993 *Emulsifiers & Detergents* (Volume 1) International Edition, both of which are published by M. C. Publishing Co. (McCutcheon Division) of Glen Rock, N.J.

The surface-active agents may be anionic, cationic, nonionic or amphoteric.

In connection with further embodiments of our present invention, a preselected 2-methyl-4-(dimethylaminomethyl)-5-hydroxybenzimidazole dihydrochloride active compound is premixed with a suitable inert solid carrier. The carrier, in turn, is combined with a suitable surface-active agent and a solvent such as water, thereby providing still another kind of dispersion that is within the contemplation of our present invention.

Alternatively, the 2-methyl-4-(dimethylaminomethyl)-5-hydroxy benzimidazole dihydrochloride active ingredient may be incorporated into a composition-of-matter wherein the carrier is in the form of granules or nodules, a paste, a dust, or a wettable powder. Accordingly, a suitable preselected 2-methyl-4-(dimethylaminomethyl)-5-hydroxybenzimidazole dihydrochloride active ingredient may advantageously be admixed with a suitable inert solid carrier, for purposes of forming a biologically-active composition-of-matter which is a solid.

Thus, for example, in the embodiment wherein a powder is formed, the solid inert carrier is provided in powder form. In many such cases the inert carrier is a mineral silicate. The solid may be made wettable by the addition of a surface active agent, well known to those skilled in the art, and referred to in the above-recited references directed to surface-active agents.

As yet another example of the scope of our present invention, the carrier component (of the biologically-active composition-of-matter of our present invention) is an aerosol. To prepare such an aerosol, a suitable preselected 2-methyl-4-(dimethylaminomethyl)-5-hydroxybenzimidazole dihydrochloride active ingredient is dissolved in a first solvent, which is conventional in the sense that although the first solvent is volatile, it is not highly volatile. The resulting solution is then admixed with a second solvent—a highly volatile solvent—the second solvent also being referrred to as a liquid aerosol carrier. The aerosol carrier is liquid only under elevated pressure. At ordinary temperatures and at atmospheric pressure, the aerosol carrier is a gas.

Further in this regard, the carrier may itself be active. For example, the carrier may be an insecticide, a herbicide, a bactericide or the like.

Among the various carriers discussed above, those comprising solvents and emulsions are particularly preferred in methods of application which utilize the anti-transpirant compositions of our present invention.

In view of the spectrum of action and the desired influences on transpiration behavior in plants and trees and in view of the many application methods possible, the agents according to this invention may be used in a large number of plants and forest species. The following crops and forest species have been found to be suitable:

| Common Name | Biological Name |
| --- | --- |
| Wheat | Triticum aestivum |
| Soybeans | Glycine max |
| Maize | Zea mays |
| Canola | Brassica napus |
| Pine | Pinus banksiana |
| Spruce | Picea mariana |

BEST MODE FOR CARRYING OUT THE INVENTION

While our present invention is susceptible to embodiment in various forms, there is hereinafter described in detail a number of examples which embody principles of our invention. This disclosure, therefore, is to be considered as merely an exemplification of our present invention without limitation to the specific embodiments or examples discussed herein.

Experimental Procedures

Four agricultural species—namely, two dicotyledonous species (soya bean cv. Maple and canola cv. Westar) and two monocotyledonous species (winter wheat cv. Harus and corn cv. 3979)—were selected for treatment. To apply seed treatments, seeds were soaked for twenty-four (24) hours in aqueous solutions of 0.01, 0.1, 1.0, 10.0, and 100 mg/l of the compounds of this invention and then sown in #16 quartz sand. Untreated seeds were also sown as controls. Seeds were germinated and grown at a temperature of 25° C./20° C. (day/night), at approximately 70 percent relative humidity (% RH), and eighteen (18) hours of 250 to 300 micromoles of photons per square meter per second of photosynthetically active radiation ($\mu$mol $m^{-2}$ $s^{-1}$ PAR).

EXAMPLE I

Imposition Of Drought By Root Misting Chambers

The root misting system consisted of two aeroponic chambers similar to those used by Robertson et al. (1985, 1990). The system was modified to incorporate a peripheral computer and customized proprietary software to control the delivery of water to the plants. The roots of the plants were sprayed with a recirculating nutrient solution—one hundred parts per million (100 ppm) nitrogen (N), as a 20.20.20 pre-formulated fertilizer (from Plant Products, Brampton, Ontario, Canada)—at pH 5.5.

The expression "20.20.20" means twenty (20) weight percent Nitrogen, 20 wt.-% Phosphorus and 20 wt.-% Potassium.

Daily adjustments were made to nutrient concentration and pH to account for plant uptake. Misting chambers were maintained with their ambient conditions similar to that of the germination environment.

Ten uniform seedlings from each of the seed-treatment concentrations were transferred to the root-misting chamber, after washing sand from the seedling roots. Within each chamber, plants were arranged randomly and were subsequently allowed to equilibrate in a two-compartment root-misting chamber for approximately seven (7) days.

After the equilibration period, drought conditions were imposed daily to plants in one or both chambers by cessation of root misting. On the first day of drought conditions, water was withheld until substantial wilting was visible in all plants. The time required to obtain the desired degree of plant wilting ranged from between two (2) hours, for canola, to six (6) hours, for corn. The controlling computer extended this original drought condition period by approximately 5% each day for the next ten (1 0) days, so that the final drought condition imposed was 50% longer than the initial drought condition imposed. At the end of the experiment, plants were harvested and a growth analysis was performed.

Because only two misting chambers were available, two uniformity trials were conducted to ensure that the misting chambers were imposing similar drought conditions. Uniformity trials were thus conducted on corn (cv. 3979) and soya bean (cv. Maple). The experimental design allowed for comparison of growth rates of treated and untreated species.

Tables I through VI, below, include data relating to responses of various plant species subjected to drought conditions, with and without treatment utilizing a preselected 2-methyl-4-(dimethylaminomethyl)-5-hydroxybenzimidazole dihydrochloride anti-transpirant active ingredient, in accordance with principles of our present invention.

The data depicts a normal biological response in that the dosage required for increased biomass is species specific.

TABLE IA

Response Of Treated Soya Beans
Subjected To Drought Conditions
Dry weight (mg)

| (mg/l) | 0.00 | 0.01 | 0.10 | 1.00 | 10.0 | 100 |
|---|---|---|---|---|---|---|
| Root | 96.82 | 109.02 | 105.10 | 97.51 | 128.55 | 124.60 |
| Stem | 216.22 | 205.17 | 222.80 | 241.28 | 267.25 | 283.85 |
| Leaf | 189.26 | 205.82 | 231.92 | 206.11 | 226.22 | 283.45 |
| Total | 499.07 | 522.69 | 557.30 | 544.45 | 622.00 | 691.90 |

TABLE IB

Response Of Treated Soya Beans
Subjected To Drought Conditions
Morphology (or morphological parameters)

| (mg/l) | 0.00 | 0.01 | 0.10 | 1.00 | 10.0 | 100 |
|---|---|---|---|---|---|---|
| Leaf Area | 58.91 | 54.72 | 63.48 | 63.13 | 67.16 | 82.10 |
| SR | 4.43 | 4.03 | 5.04 | 5.25 | 4.16 | 4.97 |
| SLA | 0.322 | 0.271 | 0.283 | 0.294 | 0.296 | 0.293 |

Notes to Tables IA and IB:
1. In Tables IA and IB, the active ingredient tested was 2-methyl-4-(dimethylaminomethyl)-5-hydroxybenzimidazole dihydrochloride. The concentration (mg/l) value listed refers to this active ingredient.
2. In Table IB, the term "SLA" means specific leaf area; and the term "SR" means shoot-to-root mass ratio.

Notes to Tables IA and IB:

1. In Tables IA and IB, the active ingredient tested was 2-methyl-4-(dimethylaminomethyl)-5-hydroxybenzimidazole dihydrochloride. The concentration (mg/l) value listed refers to this active ingredient.
2. In Table IB, the term "SLA" means specific leaf area; and the term "SR" means shoot-to-root mass ratio.

TABLE IIA

Response Of Treated Corn
Subjected To Drought Conditions
Dry Weight (mg)

| (mg/l) | 0.00 | 0.01 | 0.10 | 1.00 | 10.0 | 100 |
|---|---|---|---|---|---|---|
| Root | 856 | 1028 | 824 | 800 | — | 902 |
| Stem | 727 | 828 | 677 | 671 | — | 723 |
| Leaf | 1202 | 1323 | 1154 | 1134 | — | 1249 |
| Total | 2784 | 3180 | 2654 | 2602 | — | 2874 |

Notes to Tables IIA and IIB:
1. In Tables IIA and IIB, the active ingredient tested was 2-methyl-4-(dimethylaminomethyl)-5-hydroxybenzimidazole dihydrochloride. The concentration (mg/l) value listed refers to this active ingredient.
2. In Table IIB, the term "SLA" means specific leaf area; and the term "SR" means shoot-to-root mass ratio.

TABLE IIB

Response Of Treated Corn
Subjected To Drought Conditions
Morphology

| (mg/l) | 0.00 | 0.01 | 0.10 | 1.00 | 10.0 | 100 |
|---|---|---|---|---|---|---|
| Leaf Area | 487.35 | 519.48 | 443.63 | 456.22 | — | 504.07 |
| SR | 2.27 | 2.14 | 2.25 | 2.25 | — | 2.07 |
| SLA | 413.31 | 396.66 | 391.86 | 409.43 | — | 399.79 |

Notes to Tables IIA and IIB:
1. In Tables IIA and IIB, the active ingredient tested was 2-methyl-4-(dimethylaminomethyl)-5-hydroxybenzimidazole dihydrochloride. The concentration (mg/l) value listed refers to this active ingredient.
2. In Table IIB, the term "SLA" means specific leaf area; and the term "SR" means shoot-to-root mass ratio.

Notes to Tables IIA and IIB:

1. In Tables IIA and IIB, the active ingredient tested was 2-methyl-4-(dimethylaminomethyl)-5-hydroxybenzimidazole dihydrochloride. The concentration (mg/l) value listed refers to this active ingredient.
2. In Table IIB, the term "SLA" means specific leaf area; and the term "SR" means shoot-to-root mass ratio.

TABLE III

Growth Response Of Treated Wheat
Subjected To Drought Conditions
Dry Weight (mg)

| (mg/l) | 0.00 | 0.01 | 0.10 | 1.00 | 10.0 | 100 |
|---|---|---|---|---|---|---|
| Stressed | | | | | | |
| Root | 39.0 | 29.5 | 35.1 | 36.1 | 34.3 | 36.8 |
| Stem | 33.6 | 31.9 | 47.4 | 36.2 | 42.2 | 36.9 |
| Leaf | 69.1 | 62.7 | 78.0 | 68.4 | 76.2 | 67.0 |
| Total | 141.7 | 124.1 | 165.5 | 140.7 | 152.7 | 140.7 |
| Non-Stressed | | | | | | |
| Root | 38.7 | 30.8 | 37.4 | 22.3* | 20.7* | 19.2* |
| Stem | 33.7 | 31.3 | 32.0 | 25.6 | 21.4* | 17.8* |
| Leaf | 84.9 | 78.3 | 83.7 | 61.3 | 53.7* | 40.3* |
| Total | 157.3 | 140.4 | 153.1 | 109.2 | 95.9* | 77.3* |

Notes To Table III (Non-Stressed) Values:
(1)* = Significantly less than when treatment was 0 mg/l, non-stressed.
(2) Reported values refer to dry weight, in milligrams (mg).

TABLE IV

Morphological Response Of Treated Wheat
Subjected To Drought Conditions
Morphology

| (mg/l) | 0.00 | 0.01 | 0.10 | 1.00 | 10.0 | 100 |
|---|---|---|---|---|---|---|
| Stressed | | | | | | |
| Leaf Area | 28.90 | 19.23 | 24.27 | 18.24* | 20.82 | 19.04* |
| SR | 2.97 | 3.50 | 4.08^A | 3.50 | 3.77 | 3.31 |
| SLA | 0.309 | 0.278 | 0.318 | 0.283 | 0.355 | 0.448 |

Notes to Table IV:
(1)* = Statistically significantly less than the control (i.e. 0 mg/l).
(2)^A = Statistically significantly greater than the control (i.e. 0 mg/l).
(3)^B = Stressed, but not statistically significantly less than the control (i.e. 0 mg/l), non-stressed.

TABLE V

Growth Response Of Treated Canola
Subjected To Drought Conditions
Dry Weight (mg)

| (mg/l) | 0.00 | 0.01 | 0.10 | 1.00 | 10.0 | 100 |
|---|---|---|---|---|---|---|
| Stressed | | | | | | |
| Root | 31.48* | 35.10* | 42.36 | 37.63 | 52.03 | 36.64 |
| Stem | 35.12* | 62.65 | 79.27[A] | 66.40 | 41.16 | 46.36 |
| Leaf | 119.10 | 240.24 | 232.78 | 198.26 | 176.79 | 149.67 |
| Total | 187.35* | 333.25[B] | 348.03[B] | 281.74[B] | 272.67 | 235.21 |
| Non-Stressed | | | | | | |
| Root | 63.30 | 38.23 | 69.89 | 44.89 | 34.32* | 35.82* |
| Stem | 59.26 | 40.36 | 68.50 | 47.20 | 31.31* | 36.69* |
| Leaf | 200.85 | 136.99 | 214.68 | 132.30 | 107.85* | 111.13 |
| Total | 325.78 | 218.27 | 355.14 | 226.60 | 175.57* | 183.71 |

Notes to Tables V and VI
(1)* = Statistically significantly less than 0 mg/l, non-stressed.
(2)[A] = Statistically significantly greater than 0 mg/l, non-stressed.
(3)[B] = Stressed, but not statistically significantly less than the control value, 0 mg/l, non-stressed.

TABLE VI

Morphological Response Of Treated Canola
Subjected To Drought Conditions
Morphology

| (mg/l) | 0.00 | 0.01 | 0.10 | 1.00 | 10.0 | 100 |
|---|---|---|---|---|---|---|
| Stressed | | | | | | |
| Leaf Area | 46.98* | 83.32[B] | 87.54[B] | 70.40[B] | 69.28[B] | 70.75[B] |
| SR | 5.83 | 12.00 | 8.81 | 11.38 | 4.84 | 6.41 |
| SLA | 0.477[A] | 0.321 | 0.318 | 0.367 | 0.354 | 0.666 |
| Non-Stressed | | | | | | |
| Leaf Area | 73.91 | 49.88* | 74.39* | 43.53* | 41.22* | 40.76* |
| SR | 4.49 | 11.36 | 4.23 | 7.75 | 6.46 | 6.56 |
| SLA | 0.377 | 0.303 | 0.403 | 0.289 | 0.329 | 0.312 |

Note to Table VI (continued) non-stressed values:
(1)* = Statistically significantly less than O mg/l.

EXAMPLE 2

Wheat, Soya Bean, Corn & Canola From Treated Seeds

To evaluate the effect of the anti-transpirant agent of Example 1 upon the response of wheat subjected to dry atmospheric conditions, winter wheat seeds (cv. Harus) were treated, as described above, and allowed to germinate and grow for two (2) weeks. There were five (5) seedlings per anti-transpirant agent concentration value, which seedlings were subsequently transferred to humidity control chambers and thereafter allowed to grow for two (2) weeks under either dry or moist conditions.

Dry condition is defined as a diurnal profile of 1.5 Kpa at midnight to 2.0 KPa during the midday period. This is equivalent to 50% relative humidity ("RH") at midnight and 35% RH at midday.

Moist atmosphere is defined as 0.3 KPa at night to 0.8 KPa at midday, or 85%:70% RH night:day.

Plants were subsequently harvested and subjected to growth analyses.

Because the nature of each response to the anti-transpirant agent tested, per se, was unknown (no typical log dose response was present), the analysis of the observed data was based upon comparisons between protected pairs of "control" plants treated with 0 mg/liter anti-transpirant vis-a-vis the various concentrations of anti-transpirant agent utilized, in the presence of imposed drought conditions, using statistical analysis software "SAS" (a product of the SAS Institute, Cary, N.C.), Proc "GLM" subroutine.

Half of the agricultural species tested showed a positive response in growth, when treated with the anti-transpirant ingredient of Example 1 and thereafter subjected to drought conditions. Both the dicotyledonous species—soya bean and canola—tested exhibited a positive response.

For all species measured, there was no significant differences in the total plant weight, in view of the different anti-transpirant concentrations prior to imposition of the drought conditions. It may be concluded that the differences in mass were due to differences in growth rates, not due to any differences in mass which may have existed prior to the drought conditions being amplified during the imposed drought period.

It was seen that general pretreatment with the moderate concentrations (about 0.10 mg/l) of anti-transpirant agent mentioned above in connection with Example 1 led to an increase in the proportion of final dry weight allocated away from the root system. Such responses are typical of plants undergoing osmotic adjustment.

As can be seen upon viewing Table IA, soya beans treated as seeds with 10 mg/l and 100 mg/l of anti-transpirant ingredient—and thereafter subjected to drought conditions—exhibited 24.5% and 38.5% greater final total dry weights, respectively, than seedlings not treated thusly.

Furthermore, as can be seen upon viewing Table IB, seedlings treated with the highest level of anti-transpirant (100 mg/l) ingredient maintained a 39.3% larger leaf area. However, increase in size was not accompanied by any change in specific leaf area ("SLA") or shoot-to-root mass ratio ("SR").

It therefore may be concluded that the anti-transpirant tested affected the rate of accumulation of dry matter but not its partitioning within the plant.

As shown in Table IV, high concentrations of anti-transpirant can lead to significant reductions in growth of the unstressed plants of up to 50%, including reductions in leaf area.

That the anti-transpirant ingredient tested influenced the morphology of wheat can be seen in Table IV, principally resulting from a reduction of leaf area at high concentrations.

Treatment utilizing the anti-transpirant ingredient mentioned above (Example 1) also tended to cause more plant mass to accumulate within the plant shoot rather than the root system, leading to greater shoot-to-root ratios, as can also be seen in Table IV.

Canola seed proved to be the most responsive to seed treatments of anti-transpirant agent, leading to significantly greater growth rates during subsequent drought conditions, in comparison to untreated plants, as is shown in Table V. Drought reduced the mass of the untreated plants by 42.5% but had no significant impact on the growth of plants from seeds treated with 0.01, 0.1, and 1.0 mg/l of anti-transpirant ingredient.

Seed treated with high concentrations (100 mg/l) of anti-transpirant significantly reduced plant size in the absence of imposed drought.

However, as with wheat, the phytotoxic effect was mitigated when drought was imposed. Phytotoxicity did not target one morphological system but rather reduced the size of leaf, stem and root systems equally, leading to no change in SR and SLA, as shown in Table VI.

EXAMPLE 3

Evaluation Of Treatment Upon Canola Seed Germination

It was found that the anti-transpirant of Example 1 enhanced the germination rate of canola seeds. As can be seen in Table VII, canola seeds treated with 0.01 and 10.0 mg/l Ambiol were twice as likely to have emerged 10 days after planting than untreated seeds.

Irrespective of the final germination rate, it may be concluded from these data that the decrease in the time required for emergence of seeds treated with the compounds of this invention would enable the plants to more rapidly establish and therefore enhance the viability of the plant.

TABLE VII

The Emergence Of Treated Canola Seeds

| Anti-transpirant Concentration | Percent Emergence (days after planting) | |
| --- | --- | --- |
| (mg/l) | 10 days | 28 days |
| 0.00 | 17.7 | 85.4 |
| 0.01 | 33.3 | 75.0 |
| 0.10 | 28.1 | 84.4 |
| 1.0 | 25.0 | 69.8 |
| 10.0 | 34.4 | 89.6 |
| 100.0 | 8.3 | 79.2 |

EXAMPLE 4

Anti-Transpirant Activity On Soya Beans

Soya bean seeds (cv. G-3197) were soaked in 0, 10, or 100 mg/l of the anti-transpirant of Example 1 for twenty-four (24) hours, as outlined previously. Seeds were subsequently planted in peat pellets (Jiffy Pot #70) and grown for 4 to 6 weeks under greenhouse conditions.

One seedling of each treatment was transferred to the humidity control chambers previously described. One chamber was maintained under dry atmospheric conditions, defined as a diurnal profile of 1.5 kPa at midnight to 2.0 kPa during the midday period, equal to 50% relative humidity at midnight and 35% RH at midday.

Transpiration rates were measured by monitoring the rate of water loss for each plant, utilizing an electronic balance interfaced with an environmental control computer. The computer determined the rate of water loss or each plant by regressing ten (10) weight values, determined at ninety (90) second intervals. This information coupled with the destructive determination of the plant leaf area at the end of the sampling period enabled precise calculation of the transpiration rates.

Plants were allowed to equilibrate to experimental conditions for 12 to 18 hours, and transpiration was thereafter monitored for one complete diurnal cycle. This experiment was repeated five (5) times; and results for each set of plants were regarded as a single replicate.

As can be seen from Table VIII, treatment of soya bean seed with 10 mg/l anti-transpirant led to a significant reduction in the transpiration rates of the plants, 4 to 6 weeks after germination. The level of treatment reduced average daytime transpiration rates by 26.3% compared to plants with no anti-transpirant treatment.

The daytime activity of anti-transpirant led to a significant reduction in the total daily water usage of plants on a per leaf area basis, reducing plant water flux by 21.75% compared to the untreated plants.

When treated with 10 mg/l anti-transpirant in a similar fashion, nightime transpiration rates did not show a significant reduction.

Likewise, treatment of seeds with 100 mg/l anti-transpirant had no significant influence on the water usage parameters of soya beans in terms of daytime or nighttime transpiration or daily water usage, as is shown in Table VIII.

From this data, it is apparent that the anti-transpirant agent utilized is effective as an anti-transpirant on soya been seed at the 10 mg/l level.

The anti-transpirant utilized did not appear to be functioning in a manner similar to commercially-available anti-transpirants which coat or physically plug leaf stomata. In particular, the anti-transpirant was applied before the development of any leaf tissue and hence could not be functioning in this manner.

Also, the lack of a significant difference in the rate of water loss during the night hours further suggests a physiological, rather than physical, influence on the soya beans. Further evidence that the anti-transparent utilized is functioning at the stomatal level is seen by no change of the water loss pattern during the night period, when the stomata are closed.

EXAMPLE 5

Effect On Physiological Condition Of Conifer Seedlings

Jack Pine Seedlings: Six-month old, container-grown jack pine seedlings obtained from Forestry Canada's Petawawa National Forestry Institute were treated over a two-month period with the anti-transpirant of Example 1. Treatments consisted of the application of this anti-transparent both as a foliar spray on the tree needles and as a root drench, on a weekly basis. The anti-transpirant was applied, as described above, at increasing concentrations of 0.1, 1.0 and 10.0 mg/l. (Untreated seedling were used as controls.) Concentrations were achieved by diluting concentrated solution with distilled water.

Two months after treatment, the seedlings were subjected to imposed drought conditions, by withholding water for a seven-day period. After seven (7) days, the seedlings were subjected to drought conditions which brought the plants close to their wilting points. As the seedlings reached their wilting points, the imposed drought conditions were alleviated by re-watering the seedlings.

Physiological characteristics such as net photosynthetic rate ("Pn"), transpiration rate ("Tl"), stomatal conductance ("Cs"), needle water potential ("$\Psi_{NEEDLE}$") and water use efficiency ("WUE") were monitored before, during, and after the imposed drought conditions.

Pn, Tl, Cs, and WUE values were measured using a Li-Cor Li 6200 Portable Photosynthesis System. Needle pressure potential was measured using a Scholander-type pressure chamber.

It was found that before imposed drought, seedling plants treated with the anti-transpirant of Example 1 had significantly lower Pn and TI values, as compared to the control plants. The anti-transpirant of Example 1 had a greater effect on reducing the TI value than the Pn value, thereby causing an increase in the WUE value, before the imposition of drought conditions. The results, presented in Table IX (Part A), show the anti-transpirant properties of 2-methyl-4-(dimethylaminomethyl)-5-hydroxybenzimidazole dihydrochloride on container-grown jack pine seedlings.

After four (4) days without water, plants treated with concentrations of 2-methyl-4-(dimethylaminomethyl)-5-hydroxybenzimidazole dihydrochloride at the 1.0 g/l and 10.0 g/l levels had significantly lower Pn and TI values than the control (untreated) plants and those treated at the 0.1 mg/l level.

Data presented in Table IX (Part A), indicate that higher concentrations (1.0 and 10.0 g/l) of the anti-transpirant, 2-methyl-4-(dimethylaminomethyl)-5-hydroxybenzimidazole dihydrochloride, induce a greater reduction in Pn and TI values under mild drought. A treatment concentration of 0.1 g/l did not result in a significant increase in these factors. After seven days of drought, values in all treatment cases approached zero.

Within one (1) day after re-watering, WUE values in treated seedlings were significantly higher, as compared with untreated seedlings. (See Table IX, Part B.) Treated plants maintained higher WUE values two (2) days later, although treatment did not vary significantly. (See Table IX, Part A.)

When measured three (3) days later, all four treatments had returned to initial, pre-stress values.

Black Spruce Seeds: Black spruce seeds from ten (10) open pollinated, half-sib families were obtained from Forestry Canada's Petawawa National Forestry Institute, and were treated with the anti-transpirant, 2-methyl-4-(dimethylaminomethyl)-5-hydroxybenzimidazole dihydrochloride, as a seed soak, for a 24-hour period in concentrations of 0.1 g/l, 1.0 g/l, and 10 mg/l. (A seed soak which included no anti-transpirant was utilized as a "control.") Following treatment, the seeds were allowed to germinate in a 3:1:1 mixture (weight ratios) of peat:perlite:vermiculite and were subsequently permitted to grow for four months.

During this growth period, seedlings were treated with the anti-transpirant, 2-methyl-4-(dimethylaminomethyl)-5-hydroxybenzimidazole dihydrochloride, on a weekly basis. The morphological characteristics of root-collar diameter ("RCD") and height ("HT") were measured in ten (10) black spruce families, at the end of the four (4) month experimental period.

In fact, morphological characteristics were studied on 15–30 seedlings (depending on availability) of each of ten (10) families.

Morphological results have been analyzed and are presented in Table IX, Part C. The results show that with all black spruce families grouped together, plants treated with the anti-transpirant, 2-methyl-4-(dimethylaminomethyl)-5-hydroxybenzimidazole dihydrochloride, had significantly greater RCD values relative to the control plants. Although there were variations in the positive responses in certain families of seedlings, it appears that the compounds of our present invention promote growth in black spruce seedlings. There were no significant differences in height between seedlings treated with different concentrations of the compounds of this invention.

TABLE VIII

Transpiration Of 4-to-6 Week-Old Soya Bean Plants Treated As Seeds With Various Concentrations Of The Anti-Transpirant 2-Methyl-4-(Dimethylaminomethyl)-5-Hydroxybenzimidazole Dihydrochloride

| | Levels Of Treatment (mg $l^{-1}$) | | |
|---|---|---|---|
| | 0 | 10 | 100 |
| Day Time Transpiration Rate (mg $m^{-2}$ $s^{-1}$) | 38.67 | 28.50* | 35.40 |
| Night Time Transpiration Rate (mg $m^{-2}$ $s^{-1}$) | 7.53 | 6.60 | 8.18 |
| Daily Water Usage (g $cm^{-2}$ $day^{-1}$) | 0.21 | 0.16* | 0.19 |

Note:* = Statistically significantly different from the control at P is less than 0.01.

TABLE IX

| | 0.0 | 0.1 | 1.0 | 10.0 |
|---|---|---|---|---|
| Effects of Ambiol on Pn, Tl and WUE | | | | |

Part A:

Pn (µmol/sq.m/s)

| | | | | |
|---|---|---|---|---|
| before stress | 1.015 | 0.686 | 0.764 | 0.722 |
| mild stress | 0.733 | 0.010 | 0.348 | 0.314 |
| after stress | 0.937 | 0.750 | 0.879 | 0.678 |

Tl (µmol/sq.m/s)

| | | | | |
|---|---|---|---|---|
| before stress | 1319.0 | 818.8 | 856.0 | 512.1 |
| mild stress | 610.2 | 768.2 | 140.1 | 208.3 |
| after stress | 796.5 | 441.1 | 677.4 | 419.2 |

WUE

| | | | | |
|---|---|---|---|---|
| before stress | 0.000848 | 0.000950 | 0.000990 | 0.001474 |
| mild stress | 0.001846 | 0.001501 | 0.003169 | 0.001867 |
| after stress | 0.001342 | 0.001790 | 0.001483 | 0.001613 |

Effect Of Ambiol On Water Use Efficiency

Part B:

| 1.580 | 2.356 | 2.125 | 2.411 |
|---|---|---|---|

Effect Of Ambiol On Root Collar Diameter (mm)

Part C:

| .081 | 1.305 | 1.157 | 1.327 |
|---|---|---|---|

Our invention has been described with reference to certain preferred embodiments; and alternatives, changes and modifications may become apparent to those skilled in the art upon reading the foregoing detailed description. Any such alternative, change or modification is to be considered as forming a part of our present invention insofar as such fall within the spirit and scope of the accompanying claims.

We claim:

1. A method of using a compound of the structural formula

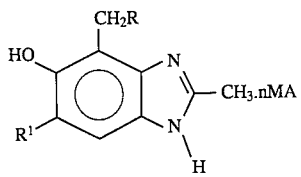

wherein:
nMa connotes that the hydroxybenzimidazole derivative structurally presented above is a mineral acid salt; n is an integer 1 through 6; MA is a mineral acid selected from the group consisting of $HNO_3$, $H_2SeO_4$, $HClO_4$, $HBrO_4$, $HMnO_4$, $HSO_3F$, $H_2SO_4$, $H_2S_2O_7$, $H_3PO_4$, $H_3BO_3$, HF, HCl, HBr, HI, and mixtures thereof: R is hydrogen, dimethylamino, piperidinyl or morpholino: and $R^1$ is hydrogen or dimethylaminomethyl, comprising applying a drought resistance enhancing amount of at least one of the above mentioned compounds to plants or seeds in need of having their drought resistance increased.

2. The method of claim 1 wherein n is 1 or 2 and the mineral acid is HBr or HCl.

3. The method of claim 1 wherein R is dimethylamino and $R^1$ is hydrogen.

4. The method of claim 1, wherein the seeds are those of legume and grain crops.

5. The method of claim 1, wherein the seeds are those of woody species.

6. A method of using a compound of the structural formula

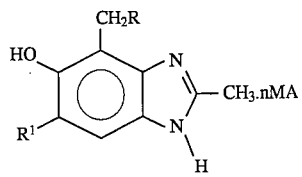

wherein:
nMa connotes that the hydroxybenzimidazole derivative structurally presented above is a mineral acid salt; n is an integer 1 through 6; MA is a mineral acid selected from the group consisting of $HNO_3$, $H_2SeO_4$, $HClO_4$, $HBrO_4$, $HMnO_4$, $HSO_3F$, $H_2SO_4$, $H_2S_2O_7$, $H_3PO_4$, $H_3BO_3$, HF, HCl, HBr, HI, and mixtures thereof: R is hydrogen, dimethylamino, piperidinyl or morpholino: and $R^1$ is hydrogen or dimethylaminomethyl, comprising applying a drought resistance enhancing amount of at least one of the above mentioned compounds to trees in need of having their drought resistance increased.

7. The method of claim 6 wherein n is 1 or 2 and the mineral acid is HBr or HCl.

8. The method of claim 6 wherein R is dimethylamino and $R^1$ is hydrogen.

* * * * *